US010752888B2

(12) United States Patent
Yang et al.

(10) Patent No.: US 10,752,888 B2
(45) Date of Patent: Aug. 25, 2020

(54) METHOD FOR ENZYMATICALLY PREPARING HIGHLY CONCENTRATED MYO-INOSITOL (71) Applicant: CJ Cheiljedang Corporation, Jung-gu, Seoul (KR)

(72) Inventors: Sungjae Yang, Suwon-si (KR); Hyun Kug Cho, Gangnam-gu (KR); Young Mi Lee, Suwon-si (KR); Seong Bo Kim, Seongnam-si (KR); Seong Jun Cho, Gwangjin-gu (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 53 days.

(21) Appl. No.: 16/314,178

(22) PCT Filed: Jun. 30, 2017

(86) PCT No.: PCT/KR2017/006983
§ 371 (c)(1),
(2) Date: Dec. 28, 2018

(87) PCT Pub. No.: WO2018/004307
PCT Pub. Date: Jan. 4, 2018

(65) Prior Publication Data
US 2019/0322991 A1 Oct. 24, 2019

(30) Foreign Application Priority Data

Jun. 30, 2016 (KR) .................. 10-2016-0082550

(51) Int. Cl.
C12N 9/12 (2006.01)
C12N 9/16 (2006.01)
C12N 9/10 (2006.01)
C12N 9/26 (2006.01)
C12N 9/34 (2006.01)
C12N 9/90 (2006.01)
C12P 7/02 (2006.01)

(52) U.S. Cl.
CPC ............ *C12N 9/16* (2013.01); *C12N 9/1051* (2013.01); *C12N 9/1205* (2013.01); *C12N 9/2414* (2013.01); *C12N 9/2428* (2013.01); *C12N 9/90* (2013.01); *C12P 7/02* (2013.01); *C12Y 204/01001* (2013.01); *C12Y 204/01007* (2013.01); *C12Y 207/01002* (2013.01); *C12Y 301/03025* (2013.01); *C12Y 302/01001* (2013.01); *C12Y 302/01003* (2013.01); *C12Y 302/01041* (2013.01); *C12Y 302/01068* (2013.01); *C12Y 505/01004* (2013.01)

(58) Field of Classification Search
CPC ....................................................... C12N 9/12
See application file for complete search history.

(56) References Cited

FOREIGN PATENT DOCUMENTS

EP         2781600 A1      9/2014
KR    10-2014-7007118     11/2012
WO    WO 2015/001312 A1   1/2015

OTHER PUBLICATIONS

Atwell, B.J. et al., "Plants in Action in Nature, Performance in Cultivation Starch and Sucrose Degradation", edition 1, MacMillan Education Australia, 1999, p. 1.
Deguchi, Michihito et al., "An engineered sorbitol cycle alters sugar composition, not growth, in transformed tobacco", Plant, Cell and Environment, 2006.
Krasensky, J. et al., "Drought, salt, and temperature stress-induced metabolic rearrangements and regulatory networks", Journal of experimental botany, 2012;63(4):1593-608.
McLaurin, J. et al., "Inositol Stereoisomers Stabilize an Oligomeric Aggregate of Alzheimer Amyloid β Peptide and Inhibit Aβ-induced Toxicity*", The Journal of Biological Chemistry, 2000.
Hansen, C. A. et al., "Synthesis of 1,2,3,4-Tetrahydroxybenzene from d-Glucose: Exploiting myo-Inositol as a Precursor to Aromatic Chemicals", Journal of the American Chemical Society, 1999.
International Search Report dated Sep. 20, 2017 in connection with PCT International Application No. PCT/KR2017/006983.
Extended European Search Report (EESR) issued by the EPO dated Jan. 7, 2020 in connection with European Patent Application No. EP 17820583.
Loewus F. A. et al., "myo-Inositol metabolism in plants", Plant Science, Elsevier Irealand Ltd, IE, vol. 150, No. 1, Jan. 14, 2000, pp. 1-19, XP002360276.
Robert h. Michell, "Inositol derivatives: evolution and functions", Nat Rev Mol Cell Bio., vol. 9, No. 2, Feb. 1, 2008, pp. 151-161, XP055348402.

*Primary Examiner* — Tekchand Saidha
(74) *Attorney, Agent, or Firm* — John P. White; Gary J. Gershik; Cooper & Dunham LLP (57) ABSTRACT

The present disclosure relates to a method for preparing myo-inositol using myo-inositol monophosphate synthase consisting of an amino acid sequence of SEQ ID NO: 1 and/or myo-inositol monophosphate phosphatase consisting of an amino acid sequence of SEQ ID NO: 3.

8 Claims, 3 Drawing Sheets
Specification includes a Sequence Listing.

METHOD FOR ENZYMATICALLY PREPARING HIGHLY CONCENTRATED MYO-INOSITOL

CROSS-REFERENCE TO RELATED APPLICATIONS

This application is a § 371 national stage of PCT International Application No. PCT/KR2017/006983, filed Jun. 30, 2017, claiming priority of Korean Patent Application No. 10-2016-0082550, filed Jun. 30, 2016, the contents of each of which are hereby incorporated by reference into the application.

REFERENCE TO A SEQUENCE LISTING

This application incorporates-by-reference nucleotide and/or amino acid sequences which are present in the file named "181228_90776_Sequence_Listing_CAS.txt", which is 16.5 kilobytes in size, and which was created Dec. 28, 2018 in the IBM-PC machine format, having an operating system compatibility with MS-Windows, which is contained in the text file filed Dec. 28, 2018 as part of this application.

TECHNICAL FIELD

The present disclosure relates to a method for preparing highly concentrated myo-inositol using myo-inositol monophosphate synthase consisting of an amino acid sequence of SEQ ID NO: 1 and myo-inositol monophosphate phosphatase consisting of an amino acid sequence of SEQ ID NO: 3.

BACKGROUND ART myo-Inositol, which is an essential ingredient in most higher animals, is widely used as a health functional material in the food, feed, cosmetic, and pharmaceutical fields. For example, myo-inositol is known to have an important role in the metabolism of cholesterol and fat, and is reported to be effective in preventing or treating hypercholesterolemia, etc. Additionally, myo-inositol has been used as a cosmetic material because it has skin functions such as moisture maintenance, sebum control, anti-aging via regulation of an antioxidant activity, etc.

Derivatives which can be synthesized using myo-inositol as a raw material have also been attracting attention as high value-added functional materials. For example, they have been reported as important mediators as major constituents of phosphoglycans for delivering insulin signals. In addition, as examples thereof, there are D-chiro-inositol and D-pinitol, which are known to be effective in treating type 2 diabetes, and scyllo-inositol, which is expected to be used as a therapeutic agent for Alzheimer's disease (2000. J Biol Chem. 275:18495-18502), a synthetic raw material of physiologically active substances (U.S. Pat. No. 5,412,080), and a synthetic raw material of liquid crystal compounds (German Patent No. 3,405,663).

Various methods for developing and improving the production process of myo-inositol on an industrial scale have been reported.

myo-Inositol is purified from rice bran, corn steep liquor, and the like by using conventional physiochemical extraction (acid, base, heat, pressure, etc.) methods known in the art. It is known that the production methods performed by direct extractions from the raw materials not only have a low yield but also possess a very low production efficiency due to difficulty in regulating yield and purity in the purification process because large amounts of various impurities are contained in the extract for each of the raw materials.

As another method, fermentative production methods have been reported for isolating and purifying myo-inositol from a fermentation broth by newly discovering strains possessing a high producibility of myo-inositol or by genetically modifying a synthetic metabolic pathway. The production strains include *Saccharomyces cerevisiae, Candida* (JP Kokai 8-00258, JP Kokai 8-38188, JP Kokai 8-89262, JP Kokai 9-117295, JP Kokai 10-42860, JP Kokai 10-42882, JP Kokai 10-42883, JP Kokai 2000-41689, JP Kokai 9-220093, JP Kokai 10-271995), *Pichia pastoris* (JP Kokai 2011-55722), and *Escherichia coli* (1999. J. Am. Chem. Soc. 121:3799-3800, International Patent No. WO2009/145838), etc. However, such fermentative methods have low productivity, and thus have not been practically applied to industrial-scale production methods.

DISCLOSURE

Technical Problem

The present inventors have made intensive efforts to develop a novel preparation method capable of producing highly concentrated myo-inositol. As a result, they confirmed that myo-inositol can be produced in high yield by using the myo-inositol monophosphate synthase and/or myo-inositol monophosphate phosphatase of the present disclosure, thereby completing the present disclosure.

Technical Solution

An object of the present disclosure is to provide a method for preparing myo-inositol using myo-inositol monophosphate synthase consisting of an amino acid sequence of SEQ ID NO: 1 and myo-inositol monophosphate phosphatase consisting of an amino acid sequence of SEQ ID NO: 3.

Advantageous Effects

The myo-inositol monophosphate phosphatase of the present disclosure, which consists of an amino acid sequence of SEQ ID NO: 3, allows myo-inositol monophosphate to be converted to myo-inositol in a very high yield within a period of time (about 85% for a 1 h reaction). Additionally, according to the method of the present disclosure, myo-inositol is produced within an extracellular enzymatic reaction buffer, and thus myo-inositol is produced at low cost compared to when myo-inositol is produced by a fermentation method using recombinant cells.

BEST MODE

Hereinbelow, the present disclosure will be described in detail. Meanwhile, each of the explanations and exemplary embodiments disclosed herein can be applied to other explanations and exemplary embodiments. That is, all combinations of various factors disclosed herein belong to the scope of the present disclosure. Furthermore, the scope of the present disclosure should not be limited by the specific disclosure provided hereinbelow.

In order to achieve the object of the present disclosure, an aspect of the present disclosure provides myo-inositol monophosphate synthase consisting of an amino acid sequence of SEQ ID NO: 1. Additionally, another aspect of the present disclosure provides myo-inositol monophosphate phosphatase consisting of an amino acid sequence of SEQ ID NO: 3.

Additionally, each of the myo-inositol monophosphate synthase and myo-inositol monophosphate phosphatase of the present disclosure may contain a peptide having a homology to the amino acid sequence of SEQ ID NO: 1 of at least 80%, 90%, 95%, 97%, or 99%. For example, it is apparent that a protein having an amino acid sequence having deletion, modification, substitution, or addition of some sequences also falls within the scope of the present disclosure as long as it has the homology and exhibits efficacy corresponding to that of the protein consisting of the amino acid sequence of SEQ ID NO: 1 or SEQ ID NO: 3.

Additionally, as long as a protein has efficacy corresponding to that of the myo-inositol monophosphate synthase of the present disclosure, which consists of the amino acid sequence of SEQ ID NO: 1, or to that of the myo-inositol monophosphate phosphatase of the present disclosure, which consists of the amino acid sequence of SEQ ID NO: 3, it does not exclude a mutation that can occur by a meaningless sequence addition upstream or downstream of the amino acid sequence of SEQ ID NO: 1 or SEQ ID NO: 3, a naturally occurring mutation, or a silent mutation. In addition, a protein including the amino acid sequence of SEQ ID NO: 1 or SEQ ID NO: 3 also belongs to the scope of the present disclosure.

Further, the myo-inositol monophosphate synthase may be encoded by the nucleotide sequence of SEQ ID NO: 2, or the myo-inositol monophosphate phosphatase may be encoded by the nucleotide sequence of SEQ ID NO: 4, but these are not limited thereto. Additionally, each of the myo-inositol monophosphate synthase and myo-inositol monophosphate phosphatase may be encoded by the nucleotide sequence having a homology of at least 80%, 90%, 95%, 97%, or 99% to the nucleotide sequence of SEQ ID NO: 2 or SEQ ID NO: 4, respectively. Based on codon degeneracy, it is apparent that proteins which consist of the amino acid sequence of SEQ ID NO: 1 or SEQ ID NO: 3, or polynucleotides which can be translated into proteins having a homology to the above proteins, can also be included in the scope of the present disclosure.

As used herein, the term "homology" refers to a degree of matching with a given amino acid sequence or nucleotide sequence, and the homology may be expressed as a percentage. In the present disclosure, a homology sequence having an activity which is identical or similar to the given amino acid sequence, or nucleotide sequence is expressed as "% homology". The homology sequence may be determined by, for example, standard software, specifically, BLAST 2.0, which calculates the parameters such as score, identity, similarity, etc., or by comparing the sequences in a Southern hybridization experiment under defined stringent conditions, and defining appropriate hybridization conditions are within the skill of the art, and may be determined by a method well known to those skilled in the art (for example, J. Sambrook et al., Molecular Cloning, A Laboratory Manual, 2nd Edition, Cold Spring Harbor Laboratory press, Cold Spring Harbor, N.Y., 1989; F. M. Ausubel et al., Current Protocols in Molecular Biology, John Wiley & Sons, Inc., New York). As used herein, the term "stringent conditions" refers to conditions that are designed to permit specific hybridization between polynucleotides. For example, these conditions are specifically described in the literature (e.g., J. Sambrook et al., supra).

In the present disclosure, the stringent conditions may be adjusted to determine the homology. In order to confirm the homology between polynucleotides, hybridization conditions of low stringency, corresponding to a $T_m$ value of 55° C., may be used. For example, a hybridization solution containing 5×SSC, 0.1% SDS, 0.25% milk, and no formamide; or a hybridization solution containing 30% formamide, 5×SSC, and 0.5% SDS may be used. Hybridization conditions of mild stringency correspond to high $T_m$ values, for example, a hybridization solution containing 40% formamide, and 5× or 6×SSC may be used. Hybridization conditions of high stringency correspond to the highest $T_m$ values, for example, a hybridization solution containing 50% formamide, and 5× or 6×SSC may be used, but the hybridization conditions are not limited to the examples above.

Hybridization requires that two nucleic acids have complementary sequences, although mismatches between bases are possible depending on the severity of hybridization. The term "complementary" is used to describe the relationship between nucleotide bases that are capable of being hybridized with each other. For example, with respect to DNA, adenosine is complementary to thymine and cytosine is complementary to guanine. Therefore, the present disclosure may also include substantially similar nucleic acid sequences as well as isolated nucleic acid fragments complementary to the entire sequence.

Specifically, the polynucleotide having homology can be detected using hybridization conditions including a hybridization step at a $T_m$ value of 55° C. and using the above-described conditions. In addition, the $T_m$ value may be 60° C., 63° C., or 65° C., but is not limited thereto. Those skilled in the art can appropriately adjust the $T_m$ value according to its purpose.

The appropriate stringency of hybridizing the polynucleotides is dependent on the length and degree of complementarity of the polynucleotides, and the variables are well known in the art. As the similarity or homology between the two nucleotides becomes greater, the $T_m$ value for hybrids of the polynucleotides having such sequence becomes even greater. The relative stability for the hybridization of the polynucleotides (corresponding to a higher $T_m$ value) decreases in the following order: RNA:RNA, DNA:RNA, DNA:DNA. The calculation formula of the $T_m$ values for hybrids, the length of which is greater than 100 nucleotides, is published in the art (Sambrook et al., supra, 9.50-9.51). For hybridization with shorter polynucleotides, e.g., oligonucleotides, the mismatch position may be more important, and the length of the oligonucleotides may determine specificity thereof (Sambrook et al., supra, 11.7-11.8).

Specifically, the polynucleotides may be detected under any one of the following hybridization conditions: 1) a salt concentration lower than 500 mM, hybridization temperature of at least 37° C.; and at least a washing step at 63° C. or higher with 2×SSPE; 2) a salt concentration lower than 200 mM and hybridization temperature of at least 37° C.; and 3) hybridization and washing at 63° C. with 2×SSPE.

The length of the hybridization nucleic acid can be, for example, at least about 10 nucleotides, 15 nucleotides, 20 nucleotides, or at least 30 nucleotides. In addition, those skilled in the art can adjust the temperature and the salt concentration in the washing solution as needed depending on the factor such as the length of the probe.

The myo-inositol monophosphate synthase and myo-inositol monophosphate phosphatase of the present disclosure may be an enzyme derived from *Thermotoga* sp., specifically may be an enzyme derived from *Thermotoga neapolitana*, but are not limited thereto.

Still another aspect of the present disclosure provides a nucleic acid encoding the myo-inositol monophosphate synthase or myo-inositol monophosphate phosphatase of the present disclosure.

Still another aspect of the present disclosure provides a transformant comprising the nucleic acid encoding the myo-inositol monophosphate synthase or myo-inositol monophosphate phosphatase of the present disclosure.

As used herein, the term "transformation" refers to a process of introducing into a host cell a vector including a nucleic acid encoding a target protein, thereby enabling the expression of the protein encoded by the nucleic acid in the host cell. For the transformed nucleic acid, it does not matter whether the transformed nucleic acid is inserted into the chromosome of a host cell and located therein or located outside the chromosome, as long as it can be expressed in the host cell, and both cases are included. Additionally, the nucleic acid includes DNA and RNA which encode the target protein. The nucleic acid may be inserted in any form as long as it can be introduced into a host cell and expressed therein. For example, the nucleic acid may be introduced into a host cell in the form of an expression cassette, which is a gene construct including all essential elements required for self-expression. The expression cassette may conventionally include a promoter operably linked to the nucleic acid, a transcription termination signal, a ribosome-binding domain, and a translation termination signal. The expression cassette may be in the form of an expression vector capable of self-replication. Additionally, the nucleic acid may be introduced into a host cell as it is and operably linked to a sequence essential for its expression in the host cell, but the nucleic acid is not limited thereto.

Additionally, as used herein, the term "operably linked" refers to a functional linkage between a promoter sequence, which initiates and mediates the transcription of the nucleic acid encoding the target protein of the present disclosure, and the above gene sequence.

The method of the present disclosure for transforming the vector includes any method of introducing a nucleic acid into a cell, and may be carried out by selecting a suitable standard technique known in the art according to a host cell. For example, examples of the method may include electroporation, calcium phosphate ($CaPO_4$) precipitation, calcium chloride ($CaCl_2$) precipitation, microinjection, a polyethyleneglycol (PEG) technique, a DEAE-dextran technique, a cationic liposome technique, and a lithium acetate-DMSO technique, but are not limited thereto.

As the host cell, it is preferable to use a host having a high efficiency of introducing DNA and a high efficiency of expressing the introduced DNA; for example, it may be *E. coli*, but is not limited thereto.

Still another aspect of the present disclosure provides a composition for producing myo-inositol, comprising the myo-inositol monophosphate synthase and myo-inositol monophosphate phosphatase of the present disclosure, a microorganism expressing the myo-inositol monophosphate synthase and myo-inositol monophosphate phosphatase of the present disclosure, or a culture of the microorganism expressing the myo-inositol monophosphate synthase and myo-inositol monophosphate phosphatase of the present disclosure.

Figure 1:
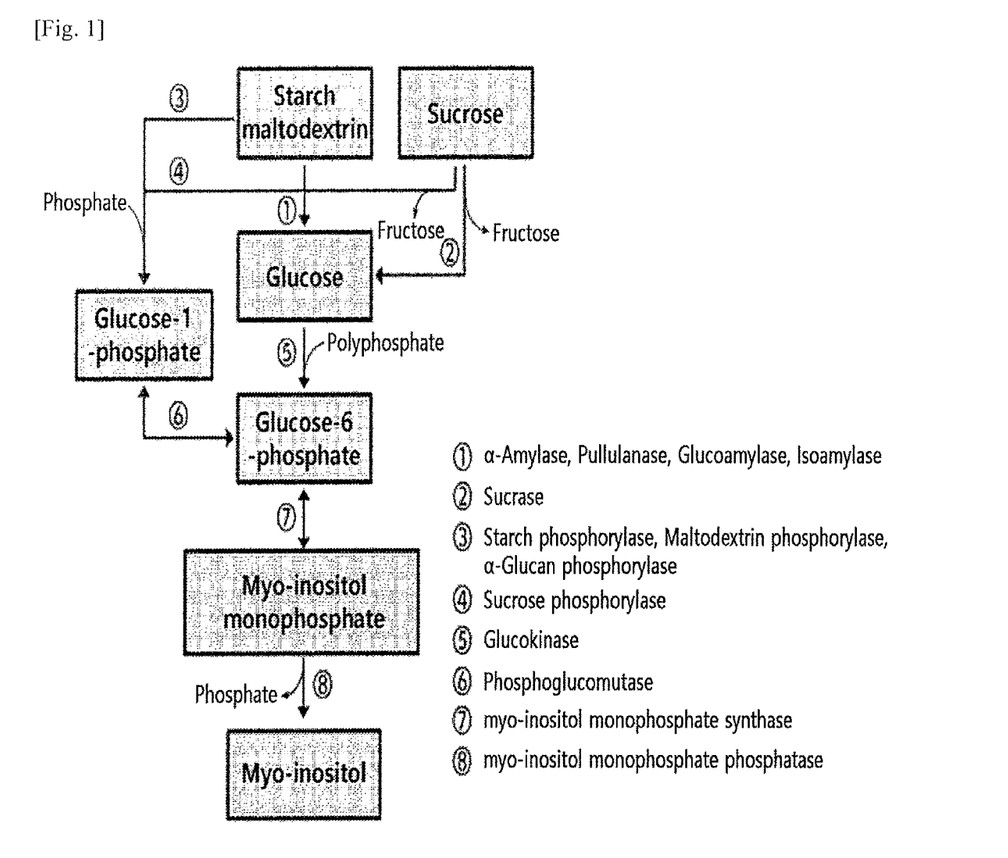
FIG. 1 is a diagram schematically showing the conversion pathway to myo-inositol, and the enzymes involved therein.

The composition of the present disclosure for producing myo-inositol may additionally include an enzyme involved in the myo-inositol preparation route of the present disclosure (see FIG. 1), a microorganism expressing the enzyme involved in the myo-inositol preparation route of the present disclosure, or a culture of the microorganism expressing the enzyme involved in the myo-inositol preparation route of the present disclosure. However, this is merely an example; that is, an enzyme to be contained in the composition of the present disclosure for producing myo-inositol and a substrate used for the production of myo-inositol are not limited, so long as the myo-inositol monophosphate synthase and/or myo-inositol monophosphate phosphatase of the present disclosure are used to produce myo-inositol.

Additionally, the composition of the present disclosure for producing myo-inositol may additionally include (a) (i) starch, maltodextrin, sucrose, or a combination thereof, glucose, glucose-1-phosphate, or glucose-6-phosphate; (ii) phosphate; (iii) phosphoglucomutase or glucokinase; and/or (iv) α-glucanophosphorylase, starch phosphorylase, maltodextrin phosphorylase, sucrose phosphorylase, α-amylase, pullulanase, isoamylase, glucoamylase, or sucrase; or (b) a microorganism expressing the enzymes or a culture of the microorganism expressing the enzymes of Item (a) above, but the composition is not limited thereto.

Specifically, the starch/maltodextrin phosphorylase (EC 2.4.1.1) and α-glucanophosphorylase of the present disclosure may include any proteins as long as these are proteins that are subjected to phosphoryl transfer from phosphate to glucose, thereby having the activity of producing glucose-1-phosphate from starch or maltodextrin. The sucrose phosphorylase (EC 2.4.1.7) of the present disclosure may include any protein as long as it is a protein that is subjected to phosphoryl transfer from phosphate to glucose, thereby having the activity of producing glucose-1-phosphate from sucrose. The α-amylase (EC 3.2.1.1), pullulanse (EC 3.2.1.41), glucoamylase (EC 3.2.1.3), and isoamylase of the present disclosure, which are enzymes for starch saccharification, may include any proteins as long as these are proteins having the activity of converting starch or maltodextrin to glucose. The sucrase (EC 3.2.1.26) of the present disclosure may include any protein as long as it s a protein having the activity of converting sucrose to glucose. The phosphoglucomutase (EC 5.4.2.2) of the present disclosure may include any protein as long as it is a protein having the activity of converting glucose-1-phosphate to glucose-6-phosphate. The glucokinase may include any protein as long as it is a protein capable of transferring phosphate to glucose, thereby having the activity of converting to glucose-6-phosphate. Specifically, the glucokinase may be a polyphosphate-dependent glucokinase, and more specifically may be a polyphosphate-dependent glucokinase derived from *Deinococcus geothermalis* consisting of the amino acid sequence of SEQ ID NO: 9 and the nucleotide sequence of SEQ ID NO: 11, or may be a polyphosphate-dependent glucokinase derived from *Anaerolinea thermophila* consisting of the amino acid sequence of SEQ ID NO: 10 and the nucleotide sequence of SEQ ID NO: 12.

Still another aspect of the present disclosure is to provide a method for preparing myo-inositol, comprising: converting myo-inositol monophosphate to myo-inositol by reacting the myo-inositol monophosphate with myo-inositol monophosphate phosphatase consisting of an amino acid sequence of SEQ ID NO: 3, a microorganism expressing the myo-inositol monophosphate phosphatase, or a culture of the microorganism expressing the myo-inositol monophosphate phosphatase. In an aspect, the preparation method of the present disclosure may further comprise converting glucose-6-phosphate to myo-inositol monophosphate by reacting the glucose-6-phosphate with myo-inositol monophosphate synthase consisting of an amino acid sequence of SEQ ID NO: 1, or a microorganism expressing the same, or a culture of the microorganism, prior to converting the myo-inositol monophosphate of the present disclosure to myo-inositol.

Still another aspect of the present disclosure provides a method for preparing myo-inositol, comprising: converting glucose-6-phosphate to myo-inositol monophosphate by reacting the glucose-6-phosphate with myo-inositol monophosphate synthase consisting of an amino acid sequence of SEQ ID NO: 1, a microorganism expressing the same, or a culture of the microorganism. In an aspect, the preparation method of the present disclosure may further comprise converting myo-inositol monophosphate to myo-inositol by reacting the myo-inositol monophosphate with myo-inositol monophosphate phosphatase consisting of an amino acid sequence of SEQ ID NO: 3, a microorganism expressing the myo-inositol monophosphate phosphatase, or a culture of the microorganism expressing the myo-inositol monophosphate phosphatase, after converting the glucose-6-phosphate of the present disclosure to myo-inositol monophosphate.

The preparation method of the present disclosure may further comprise converting glucose-1-phosphate to glucose-6-phosphate by reacting the glucose-1-phosphate with phosphoglucomutase, a microorganism expressing the same, or a culture of the microorganism, prior to converting the glucose-6-phosphate of the present disclosure to myo-inositol monophosphate.

Additionally, the preparation method of the present disclosure may further comprise converting glucose-1-phosphate to glucose-6-phosphate by reacting the glucose-1-phosphate with phosphoglucomutase, a microorganism expressing the phosphoglucomutase, or a culture of the microorganism expressing the phosphoglucomutase, prior to converting the glucose-6-phosphate of the present disclosure to fructose-6-phosphate.

Additionally, the preparation method of the present disclosure may further comprise converting starch, maltodextrin, sucrose, or a combination thereof to glucose-1-phosphate by reacting the starch, maltodextrin, sucrose, or combination thereof with phosphate and α-glucanophosphorylase, starch phosphorylase, maltodextrin phosphorylase, or sucrose phosphorylase; a microorganism expressing the phosphorylase; or a culture of the microorganism expressing the phosphorylase, prior to converting the glucose-1-phosphate of the present disclosure to glucose-6-phosphate.

Additionally, the preparation method of the present disclosure may further comprise converting starch, maltodextrin, sucrose, or a combination thereof to glucose by reacting the starch, maltodextrin, sucrose, or combination thereof with α-amylase, pullulanase, glucoamylase, sucrase, or isoamylase; a microorganism expressing the amylase, pullulanase, or sucrase; or a culture of the microorganism expressing the amylase, pullulanase, or sucrase, prior to converting the glucose of the present disclosure to glucose-6-phosphate.

The preparation method of the present disclosure may further comprise converting glucose to starch, maltodextrin, or sucrose by reacting the glucose with 4-α-glucanotransferase, a microorganism expressing the 4-α-glucanotransferase, or a culture of the microorganism expressing the 4-α-glucanotransferase.

In the preparation method of the present disclosure, the "reaction" may be carried out at a pH of 5.0 to 10.0, a temperature of 50° C. to 90° C., and/or for 1 minute to 24 hours. Specifically, the reaction of the present disclosure may be carried out at a pH of 5.0 to 9.0, a pH of 6.0 to 8.0, or a pH of 6.5 to 7.5. Additionally, the reaction of the present disclosure may be carried out at 60° C. to 80° C. or 65° C. to 75° C. Additionally, the reaction of the present disclosure may be carried out for 1 minute to 12 hours, 1 minute to 6 hours, 1 minute to 3 hours, 1 minute to 1 hour, 5 minutes to 24 hours, 5 minutes to 12 hours, 5 minutes to 6 hours, 5 minutes to 3 hours, 5 minutes to 1 hour, 10 minutes to 24 hours, 10 minutes to 12 hours, 10 minutes to 6 hours, 10 minutes to 3 hours, or 10 minutes to 1 hour.

Still another aspect of the present disclosure provides a method for preparing myo-inositol, comprising reacting starch, maltodextrin, sucrose, or a combination thereof, and phosphate with (a) myo-inositol monophosphate phosphatase consisting of an amino acid sequence of SEQ ID NO: 3; myo-inositol monophosphate synthase consisting of an amino acid sequence of SEQ ID NO: 1; phosphoglucomutase or glucokinase; and α-glucanophosphorylase, starch phosphorylase, maltodextrin phosphorylase, sucrose phosphorylase, α-amylase, pullulanase, isoamylase, glucoamylase, or sucrase; or (b) a microorganism expressing the enzyme above or a culture of the microorganism.

MODE FOR INVENTION

Hereinbelow, the present disclosure will be described in detail with accompanying exemplary embodiments. However, the exemplary embodiments disclosed herein are only for illustrative purposes and should not be construed as limiting the scope of the present disclosure.

EXAMPLE 1

Preparation of Recombinant Expression Vector Containing Genes of Myo-Inositol Monophosphate Synthase and Myo-Inositol Monophosphate Phosphatase, and Transformed Microorganism In order to provide heat-resistant myo-inositol monophosphate synthase and myo-inositol monophosphate phosphatase, which are applied to the present disclosure, each gene was separated from the thermophilic microorganism *Themotoga neapolitana*, and then each of a recombinant expression vector and a transformed microorganism were prepared.

Specifically, gene sequences related to the enzymes of the present disclosure were selected based on gene sequences of *Themotoga neapolitana* registered in Genbank. Based on the information of the amino acid sequences (SEQ ID NO: 1, myo-inositol monophosphate synthase; and SEQ ID NO: 3, myo-inositol monophosphate phosphatase) and the nucleotide sequences (SEQ ID NO: 2, myo-inositol monophosphate synthase; and SEQ ID NO: 4, myo-inositol monophosphate phosphatase), forward primers (SEQ ID NO: 5, myo-inositol monophosphate synthase; and SEQ ID NO: 6, myo-inositol monophosphate phosphatase) and reverse primers (SEQ ID NO: 7, myo-inositol monophosphate synthase; and SEQ ID NO: 8, myo-inositol monophosphate phosphatase) were devised. PCR was carried out with the synthesized primers in order to amplify each gene from chromosomal DNA (genomic DNA) of *Themotoga neapolitana*. Specifically, PCR was carried out for a total of 25 cycles under the following conditions: denaturation at 95° C. to 30 seconds, annealing at 55° C. for 30 seconds, and polymerization at 68° C. for 2 minutes. The amplified genes of the corresponding enzymes were inserted into pET21a (Novagen Inc.), which is a plasmid vector for expression in *E. coli*, using restriction enzymes NdeI and XhoI, and then recombinant expression vectors named as CJ_tn_isyn (myo-inositol monophosphate synthase-expressing plasmid) and CJ_tn_t6pp (myo-inositol monophosphate phosphatase-expressing plasmid) were constructed. CJ_tn_isyn and CJ_tn_t6pp were transformed into the *E. coli* strain BL21 (DE3) by a conventional transformation method (Sambrook et al. 1989) to prepare transformed microorganisms, which are designated as *E. coli* BL21(DE3)/CJ_tn_isyn and *E. coli* BL21 (DE3)/CJ_tn_t6pp.

The strain *Escherichia coli* BL21 (DE3)/CJ_tn_isyn and the strain *Escherichia coli* BL21 (DE3)/CJ_tn_t6pp, which are transformed into the recombinant vectors containing the gene consisting of each of SEQ ID NO: 2 and SEQ ID NO: 4, were deposited to the Korean Culture Center of Microorganisms (KCCM), which is an international depositary authority under the Budapest Treaty, on Jun. 23, 2016, and assigned Accession Nos. KCCM11849P and KCCM11850P, respectively.

Example 2

Preparation of Recombinant Enzymes

In order to prepare recombinant enzymes (hereinafter referred to as ISYN and T6PP), *E. coli* BL21(DE3)/CJ_tn_isyn and *E. coli* BL21(DE3)/CJ_tn_t6pp were each inoculated into culture tubes containing 5 mL of LB liquid medium, and then seed culture was initiated in a shaking incubator at 37° C. until the absorbance at 600 nm reached 2.0. The seed culture solution was inoculated into a culture flask containing the LB liquid medium, and the main culture was carried out. When the absorbance at 600 nm reached 2.0, 1 mM IPTG was added to induce expression of the recombinant enzymes. The stirring rate during the culturing process was set to 200 rpm and the incubation temperature was maintained at 37° C. After centrifuging the culture solution at 4° C. at 8,000×g for 20 minutes, cells were recovered. The recovered cells were washed twice with a 50 mM Tris-HCl buffer (pH 7.0), suspended in the same buffer, and then the cells were disrupted using an ultrasonic cell disruptor. The cell debris was centrifuged at 4° C. at 13,000×g for 20 minutes, and then only the supernatant was obtained. The recombinant enzymes were purified from the supernatant using His-tag affinity chromatography. The purified recombinant enzyme solution was dialyzed with a 50 mM Tris-HCl buffer (pH 7.0), and then the resultants were used for property analysis of the enzymes.

Figure 2:
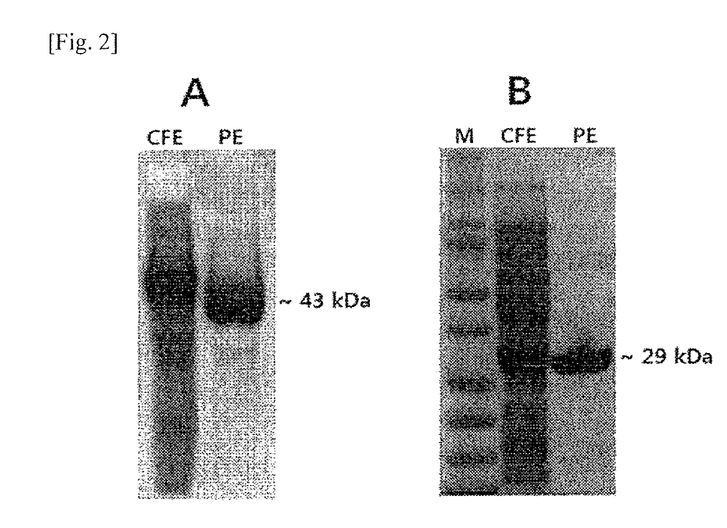
FIG. 2 shows the recombinant enzymes produced from (A) a transformant containing the enzyme of SEQ ID NO: 1 and from (B) a transformant containing the enzyme of SEQ ID NO: 3, by using chromatography. In the Figure, "M" refers to a protein size marker; "CFE" refers to a cell-free extract; and "PE" refers to a purified enzyme.

As a result, the purified recombinant myo-inositol monophosphate synthase (ISYN) and myo-inositol monophosphate phosphatase (T6PP) were analyzed by SDS-PAGE, and it was confirmed that each enzyme had the length of about 43 kDa and about 29 kDa, respectively (FIG. 2).

Example 3

Figure 3:
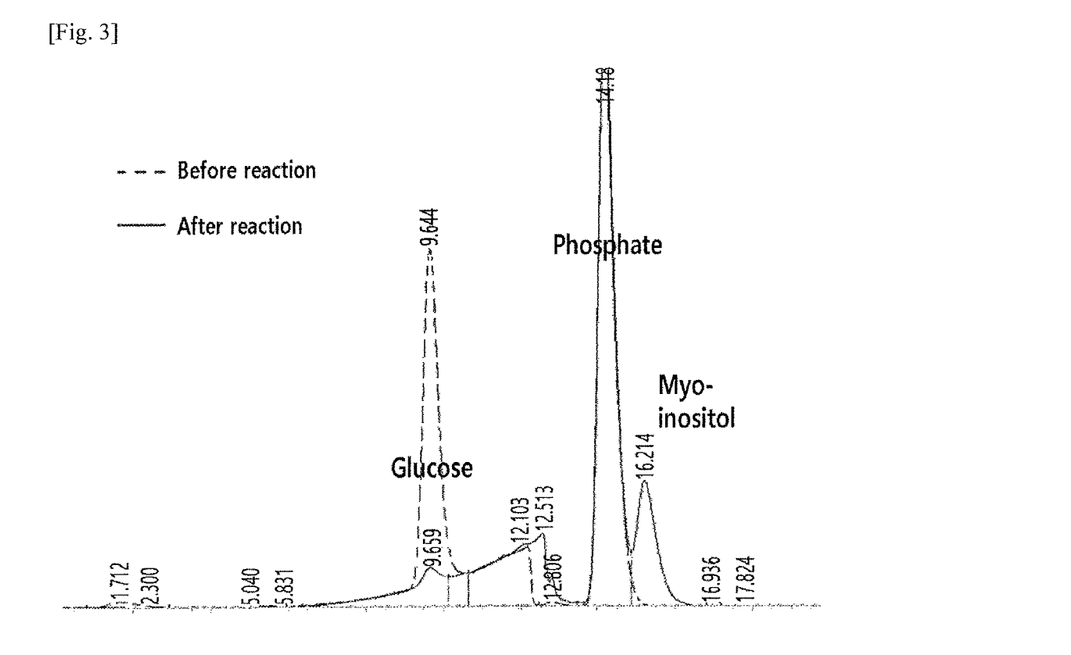
FIG. 3 is a graph showing the result of HPLC analysis, which confirms the activity of myo-inositol monophosphate synthase.

Analysis of Recombinant Enzyme Activities le;.4qGlucose-6-phosphate (50 mM) suspended in a 50 mM Tris-HCl buffer (pH 7.5) was used as the reaction composition for analyzing the activity of the myo-inositol monophosphate synthase of the present disclosure. After reacting the reaction composition with a purified enzyme (0.1 unit/mL) and glucose-6-phosphate, i.e., a substrate, at 60° C. for 1 hour, alkaline phosphatase (10 unit/mL) (NEB Inc., Calf Intestinal) was added to each reaction solution and treated at 37° C. for 1 hour, and then the reaction product was analyzed by HPLC. The HPLC analysis was carried out using an SP850 column (Shodex Inc.) while flowing the reaction product to a mobile phase at a flow rate of 0.6 mL/min at 80° C. Thereafter, glucose and myo-inositol were detected and analyzed by a Refractive Index Detector. FIG. 3 shows that the produced recombinant myo-inositol monophosphate synthase has the activity of converting glucose-6-phosphate to myo-inositol monophosphate (FIG. 3). As a result of quantitative analysis of the substrate and the products, it was confirmed that about 85% conversion was obtained after about 1 hour of the reaction.

Next, in order to analyze the activity of the myo-inositol monophosphate phosphatase of the present disclosure, glucose-1-phosphate, glucose-6-phosphate, or inositol monophosphate was used as a substrate. In addition, each substrate was used after suspension in a 50 mM Tris-HCl buffer (pH 7.0) at a concentration of 50 mM. Each reaction composition was supplemented with the purified enzymes (0.1 unit/mL), and the reaction was carried out at 70° C. for about 1 hour. Thereafter, glucose content and each phosphosugar were analyzed by HPLC.

As a result, it was confirmed that the recombinant enzyme of the present disclosure had the dephosphorylation activity only for inositol monophosphate.

Figure 4:
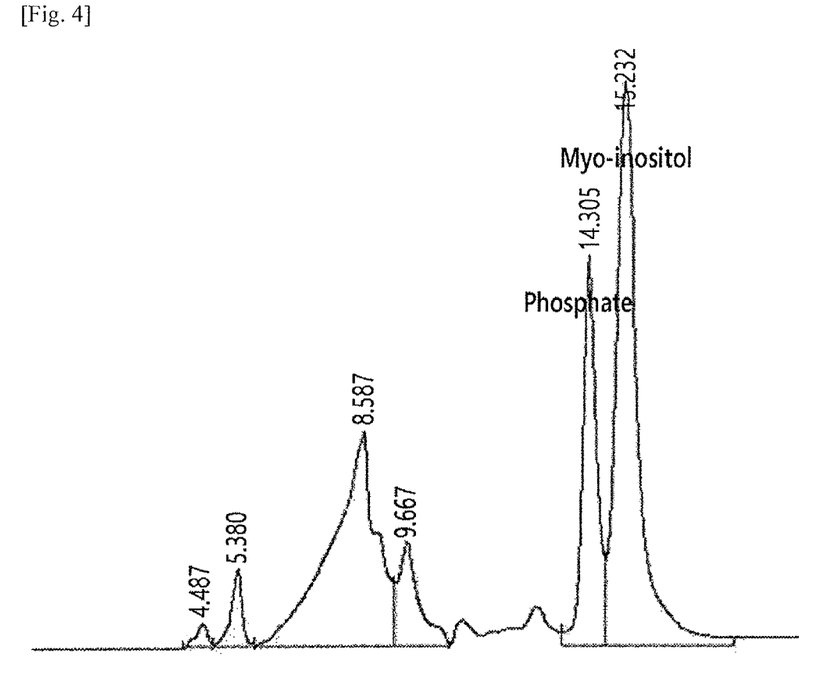
FIG. 4 is a graph showing the result of HPLC analysis, which confirms whether myo-inositol is produced from glucose-6-phosphate by simultaneously using myo-inositol monophosphate synthase and myo-inositol monophosphate phosphatase.

The myo-inositol monophosphate synthase and myo-inositol monophosphate phosphatase of the present disclosure were simultaneously used to analyze whether myo-inositol is produced from glucose-6-phosphate. As a reaction composition, the purified recombinant myo-inositol monophosphate synthase and myo-inositol monophosphate phosphatase (0.1 unit/mL), 10 mM $MgCl_2$ (or $MgSO_4$), and 50 mM glucose-6-phosphate were added and reacted at 60° C. (50 mM Tris-HCl buffer (pH 7.0)) for 1 hour to produce a reaction product, and then the reaction product was analyzed by HPLC. The HPLC analysis was carried out using an SP850 column (Shbdex Inc.) while flowing the reaction product to a mobile phase at a flow rate of 0.6 mL/min at 80° C. Thereafter, myo-inositol was detected and analyzed by a Refractive Index Detector. As a result of the analysis, it was confirmed that myo-inositol was produced in a high yield in the reaction product in which the recombinant purified enzymes were simultaneously added (FIG. 4).

While the present disclosure has been described with reference to the particular illustrative embodiments, it will be understood by those skilled in the art to which the present disclosure pertains that the present disclosure may be embodied in other specific forms without departing from the technical spirit or essential characteristics of the present disclosure. Therefore, the embodiments described above are considered to be illustrative in all respects and not restrictive. Furthermore, the scope of the present disclosure is defined by the appended claims rather than the detailed description, and it should be understood that all modifications or variations derived from the meanings and scope of the present disclosure and equivalents thereof are included in the scope of the appended claims.

The invention claimed is:

1. A method for preparing myo-inositol, comprising: converting myo-inositol monophosphate to myo-inositol by reacting the myo-inositol monophosphate with myo-inositol monophosphate phosphatase consisting of the amino acid sequence of SEQ ID NO: 3, a microorganism expressing the same, or a culture of the microorganism.

2. The method according to claim 1, wherein the method further comprises converting glucose-6-phosphate to myo-inositol monophosphate by reacting the glucose-6-phosphate with myo-inositol monophosphate synthase consisting of the amino acid sequence of SEQ ID NO: 1, a microorganism expressing the same, or a culture of the microorganism, prior to converting the myo-inositol monophosphate to myo-inositol.

3. The method according to claim 2, wherein the method further comprises converting glucose-1-phosphate to glucose-6-phosphate by reacting the glucose-1-phosphate with phosphoglucomutase, a microorganism expressing the same, or a culture of the microorganism, prior to converting the glucose-6-phosphate to myo-inositol monophosphate.

4. The method according to claim 2, wherein the method further comprises converting glucose to glucose-6-phosphate by reacting the glucose with phosphate and glucokinase, a microorganism expressing the same, or a culture of the microorganism, prior to converting the glucose-6-phosphate to myo-inositol monophosphate.

5. The method according to claim 3, wherein the method further comprises converting starch, maltodextrin, sucrose, or a combination thereof to glucose-1-phosphate by reacting the starch, maltodextrin, sucrose, or combination thereof with phosphate and α-glucanophosphorylase, starch phosphorylase, maltodextrin phosphorylase, or sucrose phosphorylase; a microorganism expressing the same; or a culture of the microorganism, prior to converting the glucose-1-phosphate to glucose-6-phosphate.

6. The method according to claim 4, wherein the method further comprises converting starch, maltodextrin, sucrose, or a combination thereof to glucose by reacting the starch, maltodextrin, sucrose, or combination thereof with α-amylase, pullulanase, glucoamylase, sucrase, or isoamylase; a microorganism expressing the same; or a culture of the microorganism, prior to converting the glucose to glucose-6-phosphate.

7. The method according to claim 1, wherein the reaction is carried out at a pH of 5.0 to 10.0, a temperature of 50° C. to 90° C., and/or for 1 minute to 24 hours.

8. A method for preparing myo-inositol, comprising reacting starch, maltodextrin, sucrose or a combination thereof, and phosphate with (a) myo-inositol monophosphate phosphatase consisting of the amino acid sequence of SEQ ID NO: 3; myo-inositol monophosphate synthase consisting of the amino acid sequence of SEQ ID NO: 1; phosphoglucomutase or glucokinase; and α-glucanophosphorylase, starch phosphorylase, maltodextrin phosphorylase, sucrose phosphorylase, α-amylase, pullulanase, isoamylase, glucoamylase, or sucrase; or (b) a microorganism expressing the enzymes, or a culture of the microorganism.

* * * * *

SEQUENCE LISTING

<160> NUMBER OF SEQ ID NOS: 12

<210> SEQ ID NO 1
<211> LENGTH: 382
<212> TYPE: PRT
<213> ORGANISM: Artificial Sequence
<220> FEATURE:
<223> OTHER INFORMATION: myo-inositol monophosphate synthase

<400> SEQUENCE: 1

| Met | Val | Lys | Val | Leu | Ile | Leu | Gly | Gln | Gly | Tyr | Val | Ala | Ser | Thr | Phe |
|---|---|---|---|---|---|---|---|---|---|---|---|---|---|---|---|
| 1 | | | | 5 | | | | | 10 | | | | | 15 | |

| Val | Ala | Gly | Leu | Glu | Lys | Leu | Lys | Lys | Gly | Glu | Ile | Glu | Pro | Tyr | Gly |
|---|---|---|---|---|---|---|---|---|---|---|---|---|---|---|---|
| | | | 20 | | | | | 25 | | | | | 30 | | |

| Val | Pro | Leu | Ala | Gly | Glu | Leu | Pro | Ile | Asp | Phe | Lys | Asp | Ile | Arg | Ile |
|---|---|---|---|---|---|---|---|---|---|---|---|---|---|---|---|
| | | 35 | | | | | 40 | | | | | 45 | | | |

| Val | Gly | Ser | Tyr | Asp | Val | Asp | Arg | Ala | Lys | Ile | Gly | Lys | Lys | Leu | Ser |
|---|---|---|---|---|---|---|---|---|---|---|---|---|---|---|---|
| | 50 | | | | | 55 | | | | | 60 | | | | |

| Glu | Val | Val | Ser | Gln | Tyr | Trp | Cys | Asp | Val | Asn | Ser | Leu | Ser | Asp | Asp |
|---|---|---|---|---|---|---|---|---|---|---|---|---|---|---|---|
| 65 | | | | | 70 | | | | | 75 | | | | | 80 |

| Pro | Val | Val | Ser | Thr | Gly | Val | His | Leu | Gly | Ser | Val | Lys | Asn | Leu | Pro |
|---|---|---|---|---|---|---|---|---|---|---|---|---|---|---|---|
| | | | | 85 | | | | | 90 | | | | | 95 | |

| Ile | Glu | Ala | Glu | Gly | Leu | Glu | Asp | Ser | Met | Thr | Leu | Lys | Glu | Ala | Ile |
|---|---|---|---|---|---|---|---|---|---|---|---|---|---|---|---|
| | | | 100 | | | | | 105 | | | | | 110 | | |

| Glu | Arg | Leu | Val | Asp | Glu | Trp | Ser | Lys | Leu | Asp | Pro | Asp | Val | Ile | Val |
|---|---|---|---|---|---|---|---|---|---|---|---|---|---|---|---|
| | | 115 | | | | | 120 | | | | | 125 | | | |

| Asn | Thr | Cys | Thr | Thr | Glu | Ala | Phe | Lys | Pro | Phe | Gly | Asn | Lys | Glu | Glu |
|---|---|---|---|---|---|---|---|---|---|---|---|---|---|---|---|
| | 130 | | | | | 135 | | | | | 140 | | | | |

| Leu | Leu | Lys | Ala | Ile | Glu | Asn | Asn | Asp | Lys | Glu | Arg | Leu | Thr | Ala | Thr |
|---|---|---|---|---|---|---|---|---|---|---|---|---|---|---|---|
| 145 | | | | | 150 | | | | | 155 | | | | | 160 |

| Gln | Val | Tyr | Ala | Tyr | Ala | Ala | Thr | Leu | Tyr | Ala | Lys | Lys | Arg | Gly | Gly |
|---|---|---|---|---|---|---|---|---|---|---|---|---|---|---|---|
| | | | | 165 | | | | | 170 | | | | | 175 | |

| Ala | Ala | Phe | Val | Asn | Val | Ile | Pro | Thr | Tyr | Ile | Ala | Asn | Asp | Pro | Ala |
|---|---|---|---|---|---|---|---|---|---|---|---|---|---|---|---|
| | | | 180 | | | | | 185 | | | | | 190 | | |

| Phe | Val | Glu | Leu | Ala | Lys | Gly | Asn | Asn | Leu | Val | Val | Phe | Gly | Asp | Asp |
|---|---|---|---|---|---|---|---|---|---|---|---|---|---|---|---|
| | | 195 | | | | | 200 | | | | | 205 | | | |

| Gly | Ala | Thr | Gly | Ala | Thr | Pro | Phe | Thr | Ala | Asp | Val | Leu | Ser | His | Leu |
|---|---|---|---|---|---|---|---|---|---|---|---|---|---|---|---|
| | 210 | | | | | 215 | | | | | 220 | | | | |

| Ala | Gln | Arg | Asn | Arg | Tyr | Val | Lys | Asp | Val | Ala | Gln | Phe | Asn | Ile | Gly |
|---|---|---|---|---|---|---|---|---|---|---|---|---|---|---|---|
| 225 | | | | | 230 | | | | | 235 | | | | | 240 |

| Gly | Asn | Met | Asp | Phe | Leu | Ala | Leu | Thr | Asp | Glu | Gly | Lys | Asn | Lys | Ser |
|---|---|---|---|---|---|---|---|---|---|---|---|---|---|---|---|
| | | | | 245 | | | | | 250 | | | | | 255 | |

| Lys | Glu | Phe | Thr | Lys | Ser | Ser | Ile | Val | Lys | Asp | Ile | Leu | Gly | Tyr | Asp |
|---|---|---|---|---|---|---|---|---|---|---|---|---|---|---|---|
| | | | 260 | | | | | 265 | | | | | 270 | | |

| Ala | Pro | His | Tyr | Ile | Lys | Pro | Thr | Gly | Tyr | Leu | Glu | Pro | Leu | Gly | Asp |
|---|---|---|---|---|---|---|---|---|---|---|---|---|---|---|---|
| | | 275 | | | | | 280 | | | | | 285 | | | |

| Lys | Lys | Phe | Ile | Ala | Ile | His | Ile | Glu | Tyr | Thr | Ser | Phe | Asn | Gly | Ala |
|---|---|---|---|---|---|---|---|---|---|---|---|---|---|---|---|
| | 290 | | | | | 295 | | | | | 300 | | | | |

| Thr | Asp | Glu | Leu | Met | Ile | Ser | Gly | Arg | Ile | Asn | Asp | Ser | Pro | Ala | Leu |
|---|---|---|---|---|---|---|---|---|---|---|---|---|---|---|---|
| 305 | | | | | 310 | | | | | 315 | | | | | 320 |

| Gly | Gly | Leu | Leu | Val | Asp | Leu | Val | Arg | Leu | Gly | Lys | Ile | Ala | Leu | Asn |
|---|---|---|---|---|---|---|---|---|---|---|---|---|---|---|---|
| | | | | 325 | | | | | 330 | | | | | 335 | |

| Arg | Lys | Glu | Tyr | Gly | Thr | Val | Tyr | Pro | Val | Asn | Ala | Phe | Tyr | Met | Lys |
|---|---|---|---|---|---|---|---|---|---|---|---|---|---|---|---|
| | | | 340 | | | | | 345 | | | | | 350 | | |

| Asn | Pro | Gly | Pro | Phe | Glu | Gly | Lys | Asn | Ile | Pro | Arg | Ile | Ile | Ala | Tyr |

```
                355                 360                 365
Glu Lys Met Arg Ile Trp Ala Gly Leu Lys Pro Lys Trp Leu
    370                 375                 380

<210> SEQ ID NO 2
<211> LENGTH: 1148
<212> TYPE: DNA
<213> ORGANISM: Artificial Sequence
<220> FEATURE:
<223> OTHER INFORMATION: myo-inositol monophosphate synthase

<400> SEQUENCE: 2
atggtcaaag tcctgattct tggtcagggc tacgttgcca gcaccttcgt tgcaggtctt      60
gaaaaactca agaagggaga gatcgaacct tacggtgtgc cgcttgcagg agaacttccg     120
atcgacttca agatatcag gatcgtggga agctacgacg tggacagggc aaagattgga     180
aagaaactga gtgaagtggt cagtcagtac tggtgtgatg tgaactctct gtccgatgat     240
cccgtcgttt ccacgggagt acaccttgga agcgtgaaga accttcccat cgaagcagaa     300
ggactcgaag acagcatgac cctgaaagag gccattgaaa ggctcgtcga tgagtggtct     360
aaactcgacc ctgacgtgat agtgaacacc tgtaccaccg aagcgttcaa gcctttcgga     420
aacaaggaag aactgctcaa agccatagaa aacaacgata agaaaggct cacagccaca     480 caggtgtacg cctacgcggc aacgttgtat gcgaaaaaac gcggtggagc agcctttgtg     540
aacggatacc gacttacata gcgaacgatc cggctttcgt cgaactcgca aagggaaca     600 atcttgtggt ctttggagac gatggagcaa cgggtgcgac cccattcacg gcagacgtgt     660
tgagccatct tgcccagagg aacaggtatg tcaaagatgt cgcacagttc aacataggtg     720
gaaacatgga ctttcttgca ctcaccgatg aaggaaagaa caagagtaaa gagttcacaa     780
agtccagtat cgtgaaagac atcctcggtt acgatgcacc gcactacata aaaccaacgg     840
gctatcttga acccctcgga gacaaaaagt tcatagcgat ccacattgag tacacgagtt     900
tcaacggtgc aaccgatgaa ctcatgataa gcggaaggat caacgacagt ccagcccttg     960
gaggtcttct tgtggatctt gtaagactcg gaaagatcgc cctcaacagg aaagagtacg    1020
gaacagtcta tcctgtgaac gccttctaca tgaagaatcc cggtccattt gaaggaaaga    1080
acataccgag gatcatcgcg tacgagaaga tgaggatctg ggcgggactg aaaccaaaat    1140
ggctgtga                                                            1148

<210> SEQ ID NO 3
<211> LENGTH: 263
<212> TYPE: PRT
<213> ORGANISM: Artificial Sequence
<220> FEATURE:
<223> OTHER INFORMATION: myo-inositol monophosphate phosphatase

<400> SEQUENCE: 3

Met Glu Gly Gly Ile Glu Leu Asp Arg Leu Asp Phe Ser Ile Lys Leu
1               5                   10                  15

Leu Arg Arg Val Gly His Phe Leu Met Leu His Trp Gly Lys Val Asp
            20                  25                  30

Ser Val Glu Lys Lys Thr Gly Phe Lys Asp Ile Val Thr Glu Ile Asp
        35                  40                  45

Lys Lys Ala Gln Glu Met Ile Val Glu Glu Ile Arg Lys Val Phe Pro
    50                  55                  60

Asp Glu Asn Ile Ile Ala Glu Glu Gly Ile Ser Glu Asn Gly Lys Lys
65                  70                  75                  80
```

```
Leu Trp Ile Ile Asp Pro Ile Asp Gly Thr Ile Asn Phe Val His Gly
                 85                  90                  95
Leu Pro Asn Phe Ser Ile Ser Ile Ala Tyr Val Glu Asn Gly Glu Val
            100                 105                 110
Lys Met Gly Val Val His Ala Pro Ala Leu Asn Glu Thr Leu Tyr Ala
        115                 120                 125
Glu Glu Asn Gly Gly Ala Phe Leu Asn Gly Glu Arg Ile Arg Val Ser
    130                 135                 140
Gly Asn Thr Ser Leu Glu Glu Cys Val Gly Ser Thr Gly Ser Tyr Val
145                 150                 155                 160
Asp Phe Thr Gly Lys Phe Ile Glu Lys Met Glu Lys Lys Thr Arg Arg
                165                 170                 175
Val Arg Ile Leu Gly Ser Ala Ala Leu Asn Ala Cys Tyr Val Gly Ala
            180                 185                 190
Gly Arg Val Asp Phe Phe Val Thr Trp Arg Ile Asn Pro Trp Asp Ile
        195                 200                 205
Ala Ala Gly Leu Ile Val Val Lys Glu Ala Gly Gly Thr Val Thr Asp
    210                 215                 220
Phe Ala Gly Lys Glu Ala Asn Val Phe Ser Lys Asn Phe Val Phe Ser
225                 230                 235                 240
Asn Gly Leu Val His Glu Glu Val Leu Glu Val Val Asn Glu Val Leu
                245                 250                 255
Lys Glu Ile Gly Glu Gly Lys
                260

<210> SEQ ID NO 4
<211> LENGTH: 792
<212> TYPE: DNA
<213> ORGANISM: Artificial Sequence
<220> FEATURE:
<223> OTHER INFORMATION: myo-inositol monophosphate phosphatase

<400> SEQUENCE: 4
atggagggag ggatcgaatt ggacagactg gacttttcga taaaactcct gagaagggtt    60
gggcactttc tcatgcttca ctggggaaag gtggacagtg tggagaaaaa gaccggtttc   120
aaagacatcg tgacggaaat agacaaaaag gcccaggaga tgatagtgga ggagatcaga   180 aaggttttc cggatgagaa cataatagcg gaggaggaa tctcggagaa cggaaaaaaa    240
ctctggataa tagatcccat agacgggacg ataaacttcg ttcatggact cccaactttt   300
tccatctcca tcgcttacgt ggagaatgga gaggtgaaga tgggagttgt gcacgctcct   360
gcactcaacg aaacactcta cgccgaagaa acgggggtg cttttttgaa cggtgaaagg   420
atcagggtgt ctggaaacac aagtcttgaa gagtgcgtgg gatcaacggg aagctatgtg   480
gatttcaccg gaaagtttat cgagaagatg gaaaagaaaa caggagagt gagaattctg   540 gggagtgcgg cgctgaacgc ctgctacgtg ggagcaggga gggtggattt cttcgtcact   600
tggaggatca atccgtggga catcgcagca ggcctgatag ttgtgaaaga ggcgggagga   660
acggtgacag attttgccgg aaaagaggca aacgttttct cgaagaattt tgtcttctcc   720
aacggactcg ttcacgaaga agttctcgaa gtggtgaacg aggttctgaa agagatagga   780 gagggaagt ga                                                        792

<210> SEQ ID NO 5
<211> LENGTH: 30
<212> TYPE: DNA
```

<210> SEQ ID NO 6
<211> LENGTH: 28
<212> TYPE: DNA
<213> ORGANISM: Artificial Sequence
<220> FEATURE:
<223> OTHER INFORMATION: myo-inositol monophosphate synthase forward primer

<400> SEQUENCE: 5
aggtaccata tggtcaaagt cctgattctt                                    30

<210> SEQ ID NO 6
<211> LENGTH: 28
<212> TYPE: DNA
<213> ORGANISM: Artificial Sequence
<220> FEATURE:
<223> OTHER INFORMATION: myo-inositol monophosphate phosphatase forward primer

<400> SEQUENCE: 6
ttttcatatg gagggaggga tcgaattg                                      28

<210> SEQ ID NO 7
<211> LENGTH: 26
<212> TYPE: DNA
<213> ORGANISM: Artificial Sequence
<220> FEATURE:
<223> OTHER INFORMATION: myo-inositol monophosphate synthase reverse primer

<400> SEQUENCE: 7
ccccctcgag cagccatttt ggtttc                                        26

<210> SEQ ID NO 8
<211> LENGTH: 27
<212> TYPE: DNA
<213> ORGANISM: Artificial Sequence
<220> FEATURE:
<223> OTHER INFORMATION: myo-inositol monophosphate phosphatase reverse primer

<400> SEQUENCE: 8
catactcgag cttcccctct cctatct                                       27

<210> SEQ ID NO 9
<211> LENGTH: 270
<212> TYPE: PRT
<213> ORGANISM: Artificial Sequence
<220> FEATURE:
<223> OTHER INFORMATION: polyphosphate-dependent glucokinase

<400> SEQUENCE: 9

Met Leu Ala Ala Ser Asp Ser Ser Gln His Gly Gly Lys Ala Val Thr
1               5                   10                  15

Leu Ser Pro Met Ser Val Ile Leu Gly Ile Asp Ile Gly Gly Ser Gly
            20                  25                  30

Ile Lys Gly Ala Pro Val Asp Thr Ala Thr Gly Lys Leu Val Ala Glu
        35                  40                  45

Arg His Arg Ile Pro Thr Pro Glu Gly Ala His Pro Asp Ala Val Lys
    50                  55                  60

Asp Val Val Val Glu Leu Val Arg His Phe Gly His Ala Gly Pro Val
65                  70                  75                  80

Gly Ile Thr Phe Pro Gly Ile Val Gln His Gly His Thr Leu Ser Ala
                85                  90                  95

Ala Asn Val Asp Lys Ala Trp Ile Gly Leu Asp Ala Asp Thr Leu Phe
            100                 105                 110

```
Thr Glu Ala Thr Gly Arg Asp Val Thr Val Ile Asn Asp Ala Asp Ala
            115                 120                 125

Ala Gly Leu Ala Glu Ala Arg Phe Gly Ala Gly Ala Gly Val Pro Gly
130                 135                 140

Glu Val Leu Leu Leu Thr Phe Gly Thr Gly Ile Gly Ser Ala Leu Ile
145                 150                 155                 160

Tyr Asn Gly Val Leu Val Pro Asn Thr Glu Phe Gly His Leu Tyr Leu
                165                 170                 175

Lys Gly Asp Lys His Ala Glu Thr Trp Ala Ser Asp Arg Ala Arg Glu
            180                 185                 190

Gln Gly Asp Leu Asn Trp Lys Gln Trp Ala Lys Arg Val Ser Arg Tyr
        195                 200                 205

Leu Gln Tyr Leu Glu Gly Leu Phe Ser Pro Asp Leu Phe Ile Ile Gly
    210                 215                 220

Gly Gly Val Ser Lys Lys Ala Asp Lys Trp Gln Pro His Val Ala Thr
225                 230                 235                 240

Thr Arg Thr Arg Leu Val Pro Ala Ala Leu Gln Asn Glu Ala Gly Ile
                245                 250                 255

Val Gly Ala Ala Met Val Ala Ala Gln Arg Ser Gln Gly Asp
            260                 265                 270

<210> SEQ ID NO 10
<211> LENGTH: 253
<212> TYPE: PRT
<213> ORGANISM: Artificial Sequence
<220> FEATURE:
<223> OTHER INFORMATION: polyphosphate-dependent glucokinase

<400> SEQUENCE: 10

Met Gly Arg Gln Gly Met Glu Ile Leu Gly Ile Asp Ile Gly Gly Ser
1               5                   10                  15

Gly Ile Lys Gly Ala Pro Val Asp Val Glu Thr Gly Gln Leu Thr Ala
            20                  25                  30

Glu Arg Tyr Arg Leu Pro Thr Pro Glu Asn Ala Leu Pro Glu Glu Val
        35                  40                  45

Ala Leu Val Val Ala Gln Ile Val Glu His Phe Gln Trp Lys Gly Arg
    50                  55                  60

Val Gly Ala Gly Phe Pro Ala Ala Ile Lys His Gly Val Ala Gln Thr
65                  70                  75                  80

Ala Ala Asn Ile His Pro Thr Trp Ile Gly Leu His Ala Gly Asn Leu
                85                  90                  95

Phe Ser Glu Lys Cys Gly Cys Pro Val Ser Val Leu Asn Asp Ala Asp
            100                 105                 110

Ala Ala Gly Leu Ala Glu Met Ile Phe Gly Ala Gly Lys Gly Gln Lys
        115                 120                 125

Gly Val Val Leu Met Ile Thr Ile Gly Thr Gly Ile Gly Thr Ala Leu
    130                 135                 140

Phe Thr Asp Gly Ile Leu Val Pro Asn Thr Glu Leu Gly His Ile Glu
145                 150                 155                 160

Ile Arg Gly Lys Asp Ala Glu Gln Arg Ser Ser Glu Ala Ala Arg Gln
                165                 170                 175

Arg Lys Asp Trp Thr Trp Gln Gln Trp Ala Lys Arg Leu Asn Glu His
            180                 185                 190

Leu Glu Arg Leu Glu Ala Leu Phe Trp Pro Asp Leu Phe Ile Leu Gly
        195                 200                 205
```

Gly Gly Ala Val Lys Asn His Glu Lys Phe Phe Pro Tyr Leu Lys Leu
    210                 215                 220

Arg Thr Pro Phe Val Ala Ala Lys Leu Gly Asn Leu Ala Gly Ile Val
225                 230                 235                 240

Gly Ala Ala Trp Tyr Ala His Thr Gln Glu Thr Gln Ala
                245                 250

<210> SEQ ID NO 11
<211> LENGTH: 813
<212> TYPE: DNA
<213> ORGANISM: Artificial Sequence
<220> FEATURE:
<223> OTHER INFORMATION: polyphosphate-dependent glucokinase

<400> SEQUENCE: 11

```
atgctggcag ccagtgacag cagccagcat ggcgggaagg ctgttacgct atctcccatg    60
agcgtgatcc tcgggattga cataggtggg agcggcatca agggggcccc tgtggacacg   120
gcaaccggga agctggtggc cgagcgccac cgcatcccca cgcccgaggg cgcgcaccca   180
gacgcggtga aggacgtggt ggttgagctg gtgcggcatt ttgggcatgc ggggccagtc   240
ggcatcactt tccctggcat cgtgcagcac ggccataccc tgagcgcagc caatgtggat   300
aaagcctgga ttggcctgga cgccgacacg cttttactg aggcgaccgg tcgcgacgtg   360
accgtgatca cgacgcaga tgccgcgggg ctagcggagg cgaggttcgg ggccggggca   420
ggtgtgccgg cgaggtgtt gctgttgacc tttgggacag gcatcggcag cgcgctgatc   480
tataacggcg tgctggtgcc caacaccgag tttgggcatc tgtatctcaa gggcgacaag   540
cacgccgaga catgggcgtc cgaccgggcc cgtgagcagg gcgacctgaa ctggaagcag   600
tgggccaaac gggtcagccg gtacctccag tatctggaag gtctcttcag tcccgatctc   660
tttatcatcg gtgggggcgt gagcaagaag gccgacaagt ggcagccgca cgtcgcaaca   720
acacgtaccc gcctggtgcc cgctgccctc cagaacgagg ccggaatcgt ggggccgcg   780
atggtggcgg cgcagcggtc acaggggac taa                                 813
```

<210> SEQ ID NO 12
<211> LENGTH: 762
<212> TYPE: DNA
<213> ORGANISM: Artificial Sequence
<220> FEATURE:
<223> OTHER INFORMATION: polyphosphate-dependent glucokinase

<400> SEQUENCE: 12

```
atggggaggc agggcatgga aattttaggg attgatatcg gaggatccgg catcaaaggg    60
gctccggtgg atgtagaaac cggccagtta accgccgagc gataccgctt acccaccccc   120
gaaaatgcct tacctgaaga agtggctctg gtagttgccc aaattgtcga acacttcag   180
tggaaaggtc gtgtaggggc aggatttcct gctgccatca gcacggcgt ggcacagacg   240
gccgcaaaca tccaccctac atggattgga cttcatgctg caaccttt cagcgaaaaa   300
tgcggatgtc ctgtctcagt gttgaatgat gcggatgctg ccggactggc ggaaatgatc   360
tttggggcag gaaaaggcca gaaaggggtg gtgctgatga ttaccattgg cactggcatc   420
gggacagccc tgttcaccga tgggatattg gtccctaata ccgagttggg acatattgaa   480
attcggggca agatgccga acagcgctct tcggaagccg cccgccagcg gaaggattgg   540
acctggcaac aatgggcaaa gcgtctgaat gagcatttgg agcgcctgga gccctgttc   600
tggcccgatt tattcatcct tggtggaggg gcagtaaaaa atcatgaaaa gttcttccct   660
```

```
tatctaaaac tgcgtactcc ctttgttgca gcaaaattgg ggaatctggc tgggattgta    720
ggcgcagcgt ggtatgctca cacccaggaa acgcaagcct ga                      762
```